United States Patent [19]
Bruder et al.

[11] Patent Number: 5,643,736
[45] Date of Patent: Jul. 1, 1997

[54] MONOCLONAL ANTIBODIES FOR HUMAN OSTEOGENIC CELL SURFACE ANTIGENS

[75] Inventors: Scott P. Bruder, Moreland Hills; Arnold I. Caplan; Stephen E. Haynesworth, both of Cleveland Heights, all of Ohio

[73] Assignees: Osiris Therapeutics, Inc., Baltimore, Md.; Case Western Reserve University, Cleveland, Ohio

[21] Appl. No.: 384,039

[22] Filed: Feb. 6, 1995

[51] Int. Cl.$^6$ .......................... G01N 33/567; C12N 5/00; C12N 5/02; C07K 16/00
[52] U.S. Cl. .......................... 435/4.21; 435/332; 435/343; 530/388.2; 530/388.7
[58] Field of Search .......................... 435/7.21, 240.2, 435/240.27; 436/63; 530/387.1, 388.1, 388.2, 388.7, 389.7, 389.1, 389.6, 391.1

[56] References Cited

PUBLICATIONS

Walsh et al, "Monoclonal antibodies with selective reactivity against osteoblasts and osteocytes in human bone" J. of Bone and Mineral Research, vol. 9, No. 11, Nov. 1994.

*Primary Examiner*—Lila Feisee
*Assistant Examiner*—Yvonne Eyler
*Attorney, Agent, or Firm*—Charles J. Herron; Elliot M. Olstein

[57] ABSTRACT

Monoclonal antibodies specific for normal human osteogenic cell subsets and the monoclonal hybridoma cell lines that synthesize and secrete these monospecific antibodies, as well as the uses of the monoclonal antibodies for diagnostic and/or therapeutic purposes.

7 Claims, 3 Drawing Sheets

MONOCLONAL ANTIBODIES FOR HUMAN OSTEOGENIC CELL SURFACE ANTIGENS

The present invention relates to the field of monoclonal antibodies, particularly monoclonal antibodies that are specific for subsets of human osteogenic cells, hybridoma cell lines that synthesize and secrete these antibodies, and the uses of the monoclonal antibodies.

Osteogenic cells are responsible for synthesizing and maintaining the extracellular matrix of both embryonic and adult bone. This family, or lineage, of cells arises from undifferentiated mesenchymal stem cells (MSCs) and progresses through a series of distinct maturational stages defined, in part, by the sequential acquisition and/or loss of specific cell surface antigens (Bruder, S. P. and Caplan, A. I., *Dev. Biol.*, 141:319–329,1990). Although monoclonal antibodies against cell surface antigens on normal cells of the osteogenic lineage have been reported for avian and rodent species (Bruder, S. P. and Caplan, A. I., *Bone*, 10:359–375, 1989; Bruder, S. P. and Caplan, A. I., *Bone*, 11:189–198, 1990; Turksen, K. et al., *J Histochem Cytochem*, 40:1339–1352, 1992), none have been reported for human cells. Some of these antibodies reported also react with cells other than those found in bone. While monoclonal antibodies have been raised against intracellular antigens in normal human osteoblasts and against the surface of transformed human osteogenic cell lines, none have recognized the surface of normal human osteoblasts (Embleton, M. J. et al., *Br J Cancer,* 43:582–587, 1981; Hosoi, S. et al., *Cancer Res,* 42:654–661, 1982; Heiner, J. et al., *Cancer Res,* 47:5377–5384, 1987; Bruland, O. et al., *Cancer Res,* 48:5302–5308, 1988; Tsai, C. et al., *Cancer Res,* 50:152–161, 1990; Walsh, S. et al., *J Bone Miner Res,* 9:1687–1696, 1994). At present, the only monoclonal antibody against a cell surface epitope capable of identifying human osteogenic cells is one directed against alkaline phosphatase (Lawson, G. et al., *Clin Chem,* 31:381–385, 1985). This well-characterized cell surface enzyme has served as the historical standard for identifying a large family of osteogenic cells, and is readily demonstrated by a simple histochemical stain. A common thread highlighted in these studies is the fact that a monoclonal antibody may also react with non-osteogenic cells while remaining a useful marker of osteogenic differentiation. So long as the monoclonal antibody is selective for cells at discrete stages of differentiation, the probe is both novel and useful.

In an experimental sense, osteogenic cells have been shown to arise from purified human mesenchymal stem cells in an in vivo setting (Haynesworth, S. E. et al., *Bone,* 13:81–88, 1992). Mesenchymal stem cells are the formative multipotential blast cells found inter alia in bone marrow, blood, dermis and periosteum that are capable of differentiating into any of the specific types of mesenchymal or connective tissues (i.e. the tissues of the body that support the specialized elements; particularly adipose, osseous, cartilaginous, elastic, and fibrous connective tissues) depending upon various influences from bioactive factors, such as cytokines. Although these cells are normally present at very low frequencies in bone marrow, a process for isolating, purifying, and greatly replicating these cells in culture, i.e. in vitro has been discovered (Haynesworth, S. E. et al., *Bone,* 13:81–88, 1992) and is the subject of another United States patent application. Finally, osteogenic cells can be derived from human mesenchymal stem cells in vitro through the addition of specific bioactive factors to the culture medium.

While the production of monoclonal antibodies by the fusion of spleen cells from immunized mice and myeloma cells grown in continuous culture has been previously described, (Kohler, et al., *Nature,* 256:495–497, 1975; Kohler, et al., *European Journal of Immunology,* 6:511–519, 1976; Galfre et al., *Nature,* 266:550–552, 1977; *Monoclonal Antibodies, Hybridomas: A New Dimension in Biological Analysis,* R. Kennett, T. McKearn, K. Bechtol, Eds., Plenum Press, N.Y. and London, 1980) and the techniques for the chemical selection of hybridomas arising from such a fusion, and the subsequent isolation of single antibody-secreting cell clones for the production of the monoclonal antibodies are also known, no cell lines, except those of Lawson et al., supra, have ever been produced that are capable of synthesizing and secreting monoclonal antibodies which selectively bind the surface of normal human osteogenic cell subsets.

The monoclonal antibodies of the present invention are selective for cell surface determinants on subsets of normal human osteogenic cells. Since the monoclonal antibodies of the present invention recognize cell surface determinants on normal human osteogenic cell subsets and mesenchymal stem cell descendents, these antibodies are effective monospecific probes for positively selecting, identifying, quantifying, and/or purifying osteogenic cells and/or cell surface antigens from tissue specimens such as bone, periosteum, marrow, or cells cultivated in tissue culture.

In one aspect, the present invention relates to hybridomas which synthesize and secrete monoclonal antibodies which react with the surface of normal human osteogenic cells but which are substantially nonreactive with other mesenchymal cells and hemopoietic cells. Examples of such hybridomas are those having ATCC accession numbers HB-11789. HB-11790 and HB-11791. Thus, the invention has provided several hybrid continuous cell lines, that produce antibody to the surface of normal human osteogenic cells, which are hybrids of a spleen cell exposed to human mesenchymal cells of the osteogenic lineage and a myeloma cell. Moreover, the present invention is also directed to the monoclonal antibodies produced by the hybridomas of the invention, as well as the particular method for producing and selecting both the hybridomas and their specific monoclonal antibodies.

In additional aspects, the present invention is directed to various methods of utilizing the monoclonal antibodies produced by the present invention for research, therapeutic and/or diagnostic purposes.

For example, the invention provides a method for detecting the presence of normal human osteogenic cell subsets in a sample comprising the steps of (a) contacting the sample with the antibody of the invention and (b) detecting the presence of normal human osteogenic cell subsets by reaction of the antibody with the sample. Also, the invention provides a method of detecting the presence of a normal human osteogenic cell in a sample which comprises (a) contacting the sample with the antibody of the invention and (b) detecting the presence of a normal human osteogenic cell by reaction of the antibody with the sample.

Also, the invention provides a method for producing a population of normal human osteogenic cells which comprises the steps of (a) contacting a cell suspension containing normal human osteogenic cells with the monoclonal antibodies of the invention and (b) recovering cells that have reacted with the monoclonal antibodies from the cell suspension. For example, the step of contacting can comprise contacting the cell suspension with solid phase linked monoclonal antibodies and the step of recovering is recovering bound cells from unbound cells.

The invention also provides a suspension of human cells comprising viable normal human osteogenic cells substantially free of other mesenchymal cells and hemopoietic cells, which can be obtained using the monoclonal antibodies of the invention.

The isolation, purification, identification and various uses of isolated human mesenchymal stem cells which can differentiate into more than one mesenchymal tissue type (e.g., bone, cartilage, muscle, tendon or marrow stroma) are fully described in copending U.S. patent application Ser. No. 08/193,262 and copending U.S. patent application docket No. 640100-29 entitled "Lineage-Directed Induction of Human Mesenchymal Stem Cell Differentiation". The entirety of each is incorporated herein by reference.

The present invention is directed to the in vitro production of monoclonal antibodies specific to human osteogenic cells in developing human bones, primary human osteogenic cell isolates in tissue culture, osteogenic cells derived from isolated, purified and culture-expanded MSCs as indicated above, as well as other potential sources of human osteogenic cells. The present invention is also directed to the use of the monoclonal antibodies and associated hybridomas (i.e. the fused myeloma-lymphocyte cells which produce the monoclonal antibodies) for diagnostic and/or therapeutic purposes. The monoclonal antibodies can be utilized not only for identifying, enumerating, localizing, and isolating human osteogenic cells and/or their antigens through various diagnostic means such as immunofluorescence, but also for delivering various pharmaceutical products and additional therapeutic uses.

The mesenchymal stem cells utilized in the invention for immunization were isolated and purified according to the procedure set forth in U.S. Pat. No. 5,486,359 with the exception that after the first passage of cells were grown to confluence, the cells were replated and exposed to Osteogenic Supplements (see Example 3) for either 3 or 6 days. Exposure of MSCs to Osteogenic Supplements for this short period, 3 to 6 days, recruits the cells into the osteogenic lineage and is effective at initiating the early events of differentiation. This treatment period was selected for the purpose of generating an immunogen consisting of, and monoclonal antibodies against, cell surface antigens which appear relatively early in the differentiation sequence. By contrast, in a current series of experiments, MSCs are exposed to Osteogenic Supplements for 12 to 16 days prior to their immunization in mice. This latter protocol is directed at generating monoclonal antibodies against cell surface antigens which emerge late in the differentiation sequence of osteogenesis.

For the purpose of these experiments, the cells were then released from the surface of the Petri dish by incubation in 0.5 mM EGTA (ethylene glycol-bis-(2-amino ethyl ether) N,N'-tetracetic acid, Sigma Chemical Co., St. Louis, Mo.) in Moscona's Salt Solution (Ca-Mg-free Tyrode's salt solution) for one hour. In this regard, because EGTA acts as a releasing agent possibly through the chelation of $Mg^{+2}$ and $Ca^{+2}$ ions, the cells were first soaked with Moscona's (a saline solution containing no $Mg^{+2}$ or $Ca^{+2}$ ions) reagent in order to remove the $Mg^{+2}$ and $Ca^{+2}$ present in the Complete Medium, and then were incubated in EGTA for one hour. The osteogenic cells were then rinsed with Tyrode's Salts (Catalog No. T-2145, without sodium bicarbonate, Sigma Chemical Co., St. Louis, Mo.), a balanced salt solution which provides certain physiological factors required for the maintenance of the structural integrity of cells in vitro, and reconstituted in Tyrode's salts for injection into a mouse for the production of antibodies. Immediately prior to immunization, the cell layer was dissociated into a single cell suspension by passage through a 20 gauge needle. A 6 week old female mouse (CB6F1/J, Jackson Labs, Bar Harbor, Me.) was immunized with the osteogenic cells by peritoneal injection according to the specific immunization protocol set forth in Example 2. Cells from several different marrow donors were used to maximize the proportion of common osteogenic cell surface antigens over donor-specific antigens. The procedure which was discovered to produce the optimal results is set forth in detail in Example 2.

Briefly, however, approximately $4-5\times10^6$ culture expanded mesenchymal stem cells exposed to Osteogenic Supplements for 3 and 6 days were intraperitoneally injected into the mouse. Separate aliquots of MSCs exposed to Osteogenic Supplements for 3 or 6 days were pooled together at the time of immunization so that the mouse received cells which had been exposed to Osteogenic Supplements for both 3 and 6 days at each immunization point. The initial injection was followed by four booster injections of such cells obtained from multiple human donors prepared in a similar fashion spaced approximately one week apart. After the 24th day, blood was drawn from the mouse and the serum from the blood was assayed by indirect immunofluorescence on frozen sections of embryonic human limbs in order to assure that the immunization regimen had been successful in generating an immune response in the mouse to the osteogenic cells.

After successfully completing the four week immunization process, the mouse was sacrificed and its spleen cells (particularly the antibody-secreting plasma cells, i.e. lymphocytes, producing antibodies with the specificity for the osteogenic cells) were fused with SP 2/0 myeloma cells (immortal antibody-secreting tumor cells obtained from Dr. Douglas Fambrough at the Carnegie Institute, Baltimore, Md.) according to the fusion procedure set forth below. The SP 2/0 myeloma cells utilized were sensitive to hypoxanthine-aminopterin-thymidine (HAT) medium by virtue of their lacking the enzyme thymidine kinase (TK). As a result, the SP 2/0 myeloma cells died when exposed to HAT selective medium. This allowed for the selection of hybrids to be accomplished by growing the fused and unfused cells in HAT medium. Moreover, in addition to the SP 2/0 myeloma cells sensitivity to HAT medium, these cells also synthesized no immunoglobulin. The benefit of using a nonimmunoglobulin secreting myeloma cell for fusion was that any immunoglobulin associated with the growth of the hybridomas arising from the fusion would indicate a genetic contribution exclusively from the immunized mouse spleen cells.

The process utilized for cell fusion to produce the hybridomas is described in detail in Example 2 below. Generally, however, the spleen cells were first mixed with a nearly equal number of the myeloma cells and centrifuged. The cell pellet was then exposed to polyethylene glycol (PEG 1500, Boehringer Mannheim, W. Germany) which promoted cell fusion. The PEG was then subsequently diluted out, and the fusion mixture was centrifuged and the pellet resuspended in specific growth medium (i.e. the HAT medium which killed the myeloma cells while permitting the growth of the hybridomas) with feeder cells (such as mouse peritoneal macrophages which aided in the establishment of hybridomas), plated into aliquots, and incubated according to the schedule set forth in Example 2. After approximately seven to ten days, small colonies of hybridoma cells (i.e. the immortalized progeny of cell fusion between the tumor cells and the β-lymphocytes found in the mouse spleen) appeared in the wells. Since the myeloma cell line utilized (i.e. SP 2/0 myeloma cells) was a mutant that had lost its ability to produce antibodies, the resultant hybridomas secreted only the antibodies designated by the antibody-secreting plasma cells (β-lymphocytes) obtained from the immunized mouse.

In order to identify those hybridoma colonies which synthesized and secreted antibodies having the specificity for osteogenic cells, a number of screening techniques (i.e. Enzyme-linked Immunosorbent Assay, Indirect Immunofluorescence Assay, etc. ) were utilized to characterize the antibodies which were secreted by the various hybridomas. The positive controls for all assays included sera from the immunized mice at various dilutions obtained at the time of spleen removal.

Since hybridoma growth was present in every one of the 960 wells seeded with cells, culture supernatants from every well were tested in the first screening assay. Human MSCs were separately grown on 96-well plates and cultured with Complete Medium, or Complete Medium with Osteogenic Supplements for 3 and 6 days. Cells were rinsed, incubated with hybridoma supernatants, then reacted with an enzyme linked secondary goat antimouse antibody. Enzyme substrate was applied, and the colored reaction product quantitated on a microplate spectrophotometer. In this way, hybridoma supernatants which selectively reacted with control MSCs, or MSCs grown in the presence of Osteogenic Supplements for either 3 or 6 days could be distinguished. Of these 960 hybridoma wells tested, 224 yielded a selective binding profile which warranted further evaluation. The detailed protocol for this semiquantitative cell-binding ELISA is described in Example 2.

The culture supernatant from colonies which were selected by the above technique were then screened against frozen sections of embryonic human limbs by indirect immunofluorescence. This assay was performed in order to identify antibodies which bound only to epitopes on normal human osteogenic cell subsets. Of the 224 wells which were selected by the semiquantitative cell-binding ELISA, only 18 of these wells tested positive for binding to the surface of a subset of normal human osteogenic cells. This characterization is important because, for the monoclonal antibodies to be utilized as a differentiation marker, they should optimally be directed to the surface of a subset of cells involved in the dynamic events of bone formation.

The hybridomas which tested positive to each of the above preliminary screens (i.e. 18 out of 960 initial wells) were then cloned by limited dilution to ensure that the subsequent analysis was performed on hybridomas which originated only from a single clone. In this regard, since multiple cell lines were likely present in the original "parent" wells, (i.e. in the original fusion well, the hybridoma cells may have descended from several fusion products and/or the spontaneous and unpredictable loss of chromosomes during the initial days after fusion resulting in additional heterogeneity) cloning of the cells was required to obtain a monoclonal hybridoma cell line. While a detailed description of the cloning process utilized is set forth below in Example 2, the cloning process basically involved the steps of replating the cells present in the original parent wells at a density of less than one cell per well. As a result of the establishment of the single cell cultures, any colony which grew in the wells was the progeny of only one replated cell. In order to assure monoclonality, multiple clonings were performed until 100% of the subclones were positive in the immunofluorescence assay for two generations.

The cell lines or clones were then propagated in tissue culture or in vivo in syngeneic or immunocompatible hosts where they continued to synthesize and secret antibodies to the osteogenic cell surface antigens. These monoclonal antibodies were then recovered from the tissue culture media or the ascites fluid by conventional techniques such as precipitation, ion exchange, affinity chromatography, etc.

The cloned hybridomas were then subsequently screened against a series of mesenchymal and non-mesenchymal derived tissues in order to identify the degree of specificity of the monoclonal antibodies to the surface of osteogenic cells. In addition, frozen sections of a variety of tissues that were obtained at surgery, therapeutic abortion, or autopsy were screened against the hybridoma culture supernatants by indirect immunofluorescence. The positive and negative reactivities were noted and are set forth in Table 4.

These data indicate that three of the hybridomas produced, identified, and cloned in accordance with the present invention (i.e. SB-10, SB-20, and SB-21) were useful for the analysis of normal human osteogenic cell subsets. All three of these hybridomas secreted antibodies which reacted to cell surface epitopes on osteogenic cells present in the normal human embryonic limb, as well as human MSCs cultured in the presence of Osteogenic Supplements. These three monoclonal antibodies were subsequently determined to be of the IgG2a, IgG1, and IgG1 isotype, respectively.

Specifically, the monoclonal antibody termed SB-10 reacts with the surface of cells present in the outer aspect of the periosteum. This is the region where osteoprogenitor cells are believed to reside, and no other molecular marker specific to these cells has been reported. SB-10 does not react with the more mature cells of the inner osteogenic collar, namely the alkaline phosphatase positive cells near the surface of the bone, and the osteocytes within the bone matrix. Two other antibodies, termed SB-20 and SB-21, react with an identical subset of osteogenic cells which is distinct from the subset with which SB-10 reacts. These cells reside within the collar of alkaline phosphatase positive cells of the developing limb. Cells immunostained by SB-10 are not stained by SB-20 or SB-21, and vice versa. Cells identified by SB-20 and SB-21 represent a subpopulation of alkaline phosphatase-positive osteoblasts, and can be found both on the surface of the newly secreted osteoid matrix, and at the interface of the overlying osteoprogenitors of the fibrous outer periosteum. Whether SB-20 and SB-21 react with the same epitope on these cells, or whether they bind two distinct antigens which are co-expressed will require a positive molecular identification of the precise antigens which each of these antibodies recognize. Since there were previously no specific cell-surface markers for normal human osteogenic cell subsets, these new monoclonal antibodies now provide effective mono-specific probes which can be utilized in identifying, quantifying, and purifying such cells, or their surface antigens, regardless of their source in the body.

The cell line cultures identified as SB-10, SB-20, and SB-21 have been deposited (in accordance with the requirement of the Budapest Treaty for patent purposes) with the American Type Culture Collection, 12301 Parklawn Drive, Rockville, Md., 20852, (deposit date Jan. 10, 1995) and are assigned the ATCC accession numbers HB-11789, HB-11790 and HB-11791, respectively.

The monoclonal antibodies produced can be labelled with suitable radioactive, enzymatic, fluorescent or other labels by conventional methods and/or bound to suitable solid carriers, which will be apparent to those skilled in the art. For example, the monoclonal antibodies can be used in combination with, or coupled to, an immunochemical such as fluorescein isothiocyanate, peroxidase, biotin and its analogs (e.g., iminobiotin), avidin and its analogs (streptavidin), or other such markers. Moreover, the monoclonal antibodies can be bound or attached to certain substrates and utilized to capture osteogenic cells when tissue samples such as bone cell isolates, periosteal biopsies, or cultured cells are brought in contact with the attached monoclonal antibodies. The bound cells may then be separated from the solid phase by known methods depending essentially upon the nature of the solid phase and the antibody. The bound cells can be recovered and used for various therapeutic purposes such as for the regeneration of bone, etc., depending upon the various external and internal factors.

As a result, the present invention contemplates any method of employing monoclonal antibodies to separate normal human osteogenic cell subsets from other cells such as fibroblastic or hemopoietic cells. For example, a further embodiment of the present invention is directed to a method of producing a population of normal human osteogenic cell subsets comprising the steps of providing a cell suspension of tissue containing such cells; contacting the cell suspension with monoclonal antibodies which recognize an epitope on the osteogenic cells but do not recognize an epitope on the fibroblastic or hemopoietic cells; and separating and recovering from the cell suspension the cells bound by the monoclonal antibodies.

In addition, an alternate embodiment of the invention is directed to a method of providing a subset of normal human osteogenic cells comprising the steps of providing a cell suspension of tissue containing such cells; contacting the cell suspension with solid-phase linked monoclonal antibodies which recognize an epitope present on the cell surface of the osteogenic cells but not on fibroblastic or hemopoietic cells; separating the unbound cells from the solid-phase linked monoclonal antibodies; and, recovering the bound cells from the solid-phase substrate.

The following examples are included for the purposes of further illustrating the present invention.

EXAMPLE 1

The Isolation, Purification and Culture Expansion of Human Mesenchymal Stem Cells Marrow Harvest Marrow was obtained by iliac aspirate from normal donors and oncology patients who were having marrow harvested for future bone marrow transplantation. All of the oncology patients had malignancies unrelated to the stromal cells and the stromal cells expressed normal karyotype.

Preparation of Marrow for Cell Culture

Aspirate marrow (5–10 ml) was transferred to sterile tubes to which 20 ml Complete Medium was added. The tubes were centrifuged at 460×g for 5 minutes to pellet the cells. The supernatant and fat layer were removed and the cell pellets (2.5–5.0 ml) were loaded onto 70% Percoll (Sigma, St. Louis, Mo.) gradients and centrifuged at 460×g for 15 minutes. The gradients were separated into three fractions with a pipet: top 25% of the gradient (low density cells-platelet fraction), pooled density=1.03 g/ml; middle 50% of the gradient (high density cells-mononucleated cells), pooled density=1.10 g/ml; and, bottom 25% of the gradient (red blood cells), pooled density=1.14 g/ml. In preliminary experiments each of these three pools were plated separately in Complete Medium in 100 mm dishes. Adherent cells were observed to be localized to the low density cells. To produce adherent cell cultures for all subsequent experiments, only the low density cells were plated.

Culturing and Passaging of Marrow-Derived Mesenchymal Stem Cells

Marrow cells from the iliac aspirate were cultured in Complete Medium (i.e. DMEM-LG medium with 10% fetal bovine serum) at 37° C. in humidified atmosphere containing 95% air and 5% $CO_2$. The cells were allowed to attach for 3 days prior to the initial medium change. Subsequent medium changes were performed every 4 days. When culture dishes became confluent, the cells were detached with 0.25% trypsin with 0.1 mM EDTA (GIBCO) for 10–15 minutes at 37° C. The action of trypsin was stopped with ½ volume fetal bovine serum. The cells were counted, split 1:3, and replated in 7 ml Complete Medium. Some aliquots of cells were cryopreserved in 90% fetal bovine serum with 10% DMSO (freezing medium).

EXAMPLE 2

Production of Cloned Hybridomas to Normal Human Osteogenic Cell Subsets

I. Immunization

A 6 week old female mouse (CB6F1/J, Jackson Labs, Bar Harbor, Me.) was initially immunized with the osteogenic cells by peritoneal injection. The initial immunization was followed by four booster injections spaced one week apart. Cells from several different marrow donors were used to maximize the proportion of common osteogenic cell surface antigens over donor-specific antigens. The procedure which was discovered to produce the optimal results is set forth in Table 1.

TABLE 1

| Background Information on MSC Donors Used in Mouse Immunization | | | |
|---|---|---|---|
| Sample # | Patient Birth Date | Clinical Diagnosis | Immunization Date |
| hMSC-17 | 10/8/57 | Breast Cancer | 5/24/94 |
| hMSC-18 | 10/17/53 | Normal donor | 6/1/94 |
| hMSC-19 | 8/1/56 | Breast Cancer | 6/7/94 |
| hMSC-20 | 1/28/66 | AML | 6/14/94 |
| hMSC-21 | 3/4/48 | Breast Cancer | 6/21/94 |

AML = Acute Myelogenous Leukemia

The Immunization Schedule

A. Day 0—The initial injection consisted of cells from donor hMSC-17 which were isolated and purified according to the procedure set forth above in Example 1. Cells from second passage were grown in the presence of Osteogenic Supplements on separate plates for either 3 or 6 days, and then released from the plates by incubating with 0.5 mM EGTA in Moscona's for one hour. The cells were pooled from both sets of conditions (3 and 6 days of exposure to Osteogenic Supplements), rinsed twice with Tyrode's, and then reconstituted in 500 µl of Tyrode's for injection into the mouse. The cell layers were dissociated to single cells by passing through a 20 gauge needle fitted on a 1 ml syringe and then injected into the peritoneal cavity of the mouse. Approximately $4.0 \times 10^6$ cells were used. All subsequent booster injections were prepared in a similar fashion.

B. Day 8—Cells were derived from donor hMSC-18 and collected after culture with Osteogenic Supplements. Total cell count=$5 \times 10^6$.

C. Day 14—Cells were derived from donor hMSC-19 and collected after culture with Osteogenic Supplements. Total cell count=$5 \times 10^6$.

D. Day 21—Cells were derived from donor hMSC-20 and collected after culture with Osteogenic Supplements. Total cell count=$5 \times 10^6$.

At day 24 blood was drawn from the tail vein of the mouse and serum was prepared by centrifugation. The serum was serially diluted, and then incubated on a frozen section of human embryonic limb for indirect immunofluorescence. The serum reacted positively to osteogenic cells in the frozen section, out to a dilution of 1:1,000,000 thereby indicating that the immunization regimen had been successful in generating an immune response in the mouse.

E. Day 28—Cells were derived from donor hMSC-21 and collected after culture with Osteogenic Supplements. Total cell count=$5 \times 10^6$.

F. Day 31—The fusion procedure was performed as outlined below.

II. Fusion

After successfully completing the four week immunization process, the immunized mouse was sacrificed and its spleen cells were fused with SP 2/0 myeloma cells obtained from Dr. Douglas Fambrough at the Carnegie Institute in Baltimore, Md., according to the specific process set forth below. However, in order to provide conditioned medium for the hybridoma cells produced during the fusion process, it was necessary to prepare a "feeder layer", comprised of peritoneal macrophages, one day prior to the fusion. The peritoneal macrophages were added to chemically condition the medium, as well as to clean the culture dishes through their phagocytic action. The following procedures were utilized to produce the feeder layer and to prepare the SP 2/0 myeloma cells for fusion.

A. Preparation of Feeder Cells

Since lymphoid cells often grow poorly or die when grown at low density (the reasons for this are not well understood, but may relate to the requirements for "growth factors" or to the problems of toxic by-products of the tissue culture vessel), the addition of a slow-growing or non-growing population of cells (usually termed "feeders") was necessary. The feeder cells utilized in the current process were produced according to the following procedure.

A 0.34M sucrose solution was filtered for sterilization and the solution was stored in 15 ml aliquots at 4° C. A mouse was sacrificed by cervical dislocation and immersed completely in 70% EtOH. After several minutes in EtOH, the mouse was removed and laid supine on a styrofoam test tube rack. A midline cut was made in the abdominal skin. Using blunt dissection, the skin was spread away from the peritoneum making sure not to puncture the thin membrane. Using a 20 gauge needle, 5 ml of sucrose was injected into the peritoneal cavity. The needle was removed and the abdomen was gently massaged in order to liberate the macrophages. A 23 gauge needle was inserted into the abdomen and the 5 ml of sucrose was slowly recovered. The peritoneal injection and abdominal massage were repeated two times and the macrophages were pooled. The cells were centrifuged for 5 minutes at 200×g on a Sorvall GLC-4 with an H1000 rotor (r=18.6 cm).

The cell pellet was resuspended in 15 ml D-MEM (Dulbecco's Modified Eagle's Medium, Gibco, Grand Island, N.Y., #430-2100)/10% FBS (Fetal Bovine Serum, Gibco, #430,2100) and centrifuged again. The pellet was then brought up in 2 ml of medium and the cells counted. An average yield was 3 to 6 million cells per mouse.

The cells were resuspended in Super HAT medium at a concentration of $1 \times 10^5$ cells/ml. In this regard, Super HAT medium consisted of 400 ml D-MEM, 120 ml FBS, 60 ml NCTC-109-Hybridoma Growth Supplement (M.A. Bioproducts #12-923A), 12 ml 50X HAT or H+T (Boehringer Mannheim #644579 or #623091, respectively), 6 ml Solution I (supplemented D-MEM to provide proper pH and enhanced growth of the hybridomas, containing 0.2 units/ml Insulin, 0.5 mM Na Pyruvate, and 1.0 mM oxaloacetic Acid), 6 ml L-Glutamine (Gibco #320-5030), 0.6 ml Gentamicin (M.A. Bioproducts #17-5182).

An 0.1 ml aliquot of the suspension was then added to each well of ten 96-well culture dishes. Ten dishes were used per fusion. The wells were stored in a 37° C. humid incubator with 5% carbon dioxide, 95% air.

B. preparation of SP 2/0 Myeloma Cells

The myeloma cells obtained from Dr. Fambrough were evaluated in order to ensure that they were growing well in culture for not less than 2 months prior to the fusion procedure. The cells were passed in DMEM (Dulbecco's Modified Minimal Eagle's medium)/10% FBS/8-Azaguanine (Gibco, Grand Island, N.Y.) in order to select for HAT sensitive cells. Passage of either myeloma or hybridoma cells was accomplished by serially diluting an aliquot across 12 wells of a 48- well plate.

Two weeks prior to fusion, the medium was step-wise adjusted up to 20% FBS. One week prior to fusion, several large flasks (75 $cm^2$, 20 ml of medium) of SP 2/0 myeloma cells were initiated. At that time two rows of a 24-well plate were seeded with SP 2/0 myeloma cells at low density. One day later, the medium was then changed in one of the rows with the same Super HAT medium which was going to be used for fusion. (Prior to using any medium, a sample from each bottle was tested for sterility and bacterial growth). Within 24 hours, most of the cells fed HAT were dead, and by 72 hours, all cells fed HAT (hypoxanthine, aminopterin, thymidine) were dead. Cells fed SP 2/0 growth medium remained healthy.

Two days before the fusion, the SP 2/0 myeloma cells were split into three new flasks at various dilutions (i.e. 1:20, 1:10, 1:4). The cells were carefully monitored at various dilutions and only those cells which were in log phase of growth were selected for fusion. There were no dead or dying cells in the selected population. A flask containing an appropriate density of log phase cells contained a total of one to ten million cells.

C. The Fusion Procedure

Two frosted glass slides were removed from 70% EtOH and placed in a sterile Petri dish under a hood so that they would air-dry. The mouse was sacrificed by cervical dislocation and immersed in 70% EtOH. After several minutes the mouse was placed on a large watch glass (with cork stand) with its left side up. A sterile 100 mm Petri dish with 5 ml D-MEM/10% FBS/2X antibiotic was set up for receiving the spleen. The skin and then the abdominal wall were opened on the left upper quadrant of the mouse. The spleen was removed and placed in the Petri dish. Using dissecting forceps, as much of the white fibrous connective tissue as possible was removed. The cleaned spleen was placed into another Petri dish with D-MEM/10% FBS/2X antibiotic.

Any residual EtOH was flame dried from the glass slides. The slides were then used to slice the spleen into three pieces. Each of these pieces was then gently ground between the frosted ends of the slides to liberate the spleen cells. The cell suspension was then aspirated with a pipet, large pieces of connective tissue sank immediately to the tip. These were then discarded and the remaining cell suspension was transferred into a sterile 50 ml centrifuge tube. Another 5 ml of D-MEM/10% FBS/2X antibiotic was added to the Petri dish and this was used to collect residual cells. The solution was pipeted as above, the cells added into a 50 ml centrifuge tube, and placed on ice.

The SP 2/0 myeloma cells were collected by centrifugation in a sterile 50 ml centrifuge tube. At the same time, the spleen cells were pelleted at 1000 rpm for 5 minutes. Both sets of cells were washed three times with 5 ml of cold, serum-free D-MEM (i.e. serum interferes with the fusion of these two cell types). Both sets of cells were then resuspended in 5 ml of ice cold serum-free D-MEM by gently tapping and pipetting. These cell suspensions were kept cold on ice.

The spleen cells were then counted using the hemocytometer. A 30 µl aliquot of cells was taken and added to 30 µl of 4% acetic acid. The acid lysed the RBCs and made it easier to count the splenocytes. The sample was applied to the hemocytometer and the cells were counted in 25 large squares. This number, X, when divided by 50 gave the concentration of cells, in millions per ml. There were approximately 120 million spleen cells total.

The fusion process was performed using a 6:5 ratio of spleen cells to SP 2/0 cells (i.e. the SP 2/0 cells were counted and approximately 100 million cells were used). The SP 2/0 cell suspension was then added to the spleen cells and the mixture was centrifuged for 5 minutes at 1000 rpm. All of the supernatant was removed thereby leaving the pellet as dry as possible. The pellet was loosened by tapping the tube briskly. It was important to break up this pellet so that the PEG would contact as many cells as possible.

The tube was then placed in a 37° C. water bath. PEG solution (the fusion promoter; 1 ml at 37° C.) was added drop wise directly onto the pellet over a full one minute-period. The tube was rotated while the PEG was added. To suspend the cells, the tube was gently swirled. The mixture was then allowed to sit in the water bath for about one minute. While rotating the tube 1 ml of 37° C. serum-free DMEM was added over a one minute period. Serum-free DMEM (20 ml at 37° C.) was then added over a four minute period. The mixture was centrifuged at 1000 rpm for five minutes. The supernatant was immediately removed and the pellet was resuspended in 100 ml Super HAT medium. An aliquot of this suspension (0.1 ml) was placed in each well of the ten plates containing the macrophages.

III. Preliminary Screens Prior to Cloning

There were two general screening methods used to characterize the antibodies that were secreted by the various hybridomas: the Semiquantitative Cell-Binding Enzyme-Linked Immunosorbent Assay (or ELISA Assay) and the Indirect Immunofluorescence Assay. Culture supernatant from colonies that were identified on the basis of selective cell surface binding in the semiquantitative ELISA were then screened against frozen sections of 55–70 day embryonic human limbs by indirect immunofluorescence. This assay system was designed to identify antibodies which bound to epitopes on normal human osteogenic cells. What follows is a summary of how these assays were used to screen the hybridoma colonies present in the 960 wells for those hybridomas which produce antibodies with specificity for normal human osteogenic cell subsets.

Semiquantitative Cell-Binding ELISA

Culture-expanded human MSCs were plated into each well of 30 96-well plates. Ten plates were fed only Complete Medium, while ten each of the other 20 plates were fed Complete Medium with Osteogenic Supplements for either 3 or 6 days, respectively. On the day of the assay, the plates were collected, the media was removed, and the cell layers were washed with PBS. The plates were then blocked for 30 minutes with 1% BSA in PBS, pH 7.4. Supernatants were collected from every well of the hybridoma plates, and 50 µl was added to each of the three MSC preparations describd above. Supernatants were incubated with the cells for one hour at 4° C. The plates were rinsed three times with PBS, and subsequently incubated with 100 µl of goat anti-mouse horseradish peroxidase conjugated secondary antibody (Southern Biotechnology, Inc.) diluted 1:1000 in PBS with 0.1% BSA for one hour at 4° C. The plates were then rinsed three times with PBS, and incubated with 100 µl of enzyme substrate (5 mg ortho-phenylenediamine, 8 µl 30% hydrogen peroxide, 12.5 ml sodium phosphate OPD buffer, pH 6.5) for 30 minutes.

A colorimetric reaction product was formed in some wells, depending on the amount of secondary antibody binding, which was quantified by scanning every well of every plate in a microplate spectrophotometer set for the 590 nm wavelength. Binding profiles for each hybridoma colony were generated, based on the quantitaive binding to each of the three cell preparations (MSCs cultured in Complete Medium, and MSCs cultured with Osteogenic Supplements for either 3 or 6 days). In this way, hybridomas were chosen which selectively bound MSCs cultured under specific conditions. See Table 2 for examples of binding profiles.

TABLE 2

Immunoreactivity of selected hybridoma colonies against untreated MSCs, or MSCs cultured with Osteogenic Supplements (OS) for 3 or 6 days

| Cell Line | Untreated MSCs | OS for 3 days | OS for 6 days |
| --- | --- | --- | --- |
| SB-10 | 6 | 2 | 1 |
| SB-20 | 0 | 3 | 5 |
| SB-21 | 0 | 2 | 4 |
| SB-1* | 0 | 0 | 0 |

*negative control

Numbers reflect the relative amount of primary monoclonal antibody bound in the ELISA assay described above.

Staining of Cryosections

Cryosections of unfixed 55–70 day human embryonic limbs, or other tissues of interest, were removed from the freezer and allowed to warm to room temperature before using. The sections were covered with 50–100 μl of hybridoma culture supernatant and incubated at room temperature for one hour in a humidified chamber. The slides were rinsed four times with 0.1% BSA- PBS. The sections were then covered with 50 μl of FITC-conjugated Goat anti-mouse IgG (Organon Teknika, Catalog #1211-0231) which had been diluted 1:500 with 0.1% BSA-PBS. These slides were allowed to incubate for one hour at room temperature in a humidified chamber. The slides were rinsed four times with 0.1% BSA-PBS and coverslipped with a drop of PPD immunofluorescence mounting medium, and observed with an Olympus B-Max epi-fluoresence microscope. Negative control slides were incubated with culture medium which did not contain antibody, followed by the routine subsequent steps.

Figure 1:
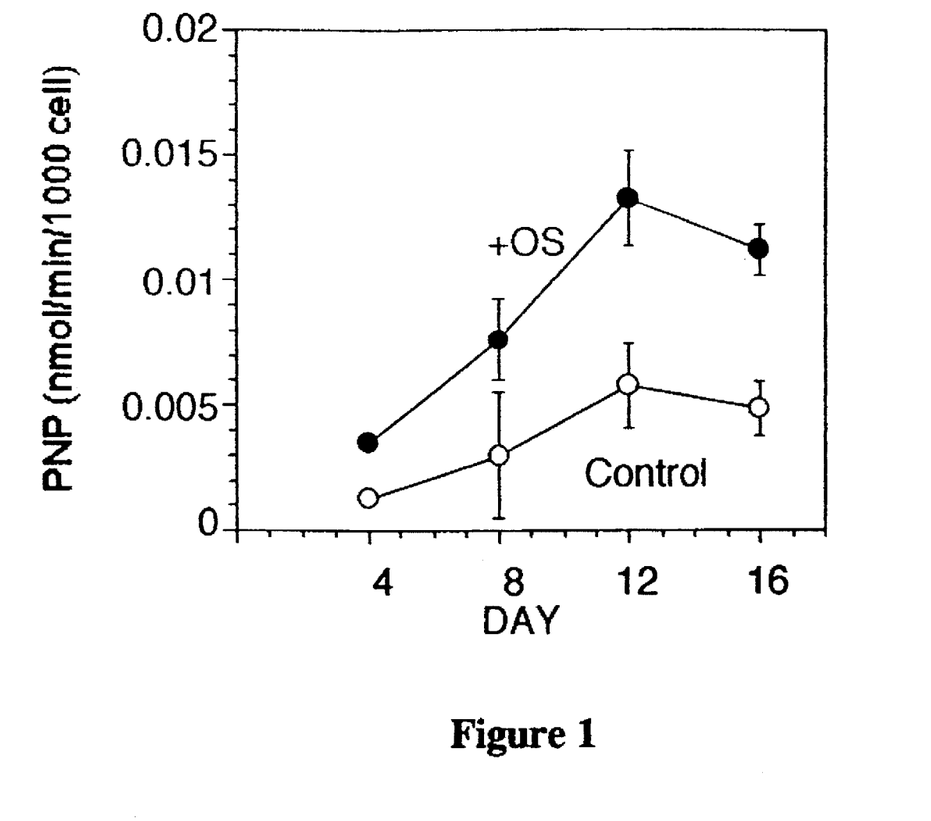
FIG. 1 is a graphical representation of alkaline phosphatase enzyme activity in human MSC cultures grown in Complete Medium with and without the presence of Osteogenic Supplements for up to 16 days.
Figure 2A:
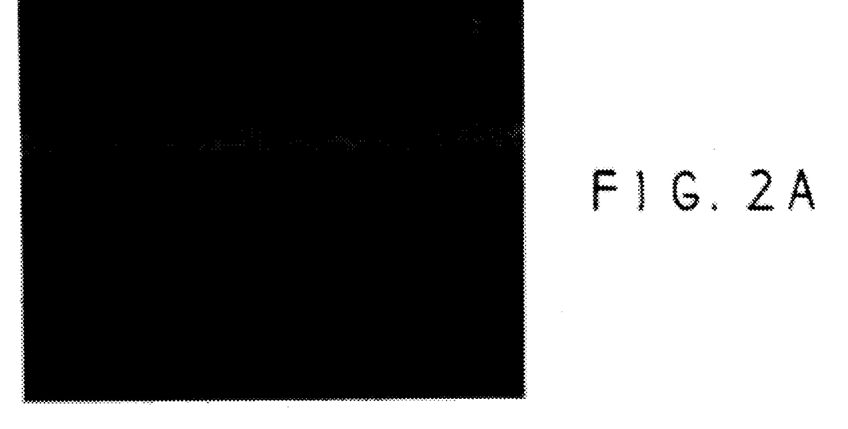
FIGS. 2A–2F are photomicrographs of a 57 day embryonic human limb stained with monoclonal antibodies SB-10 (A), SB-20 (C), and SB-21 (F). Panels B, D and F provide the phase contrast image for each of the immunofluorescent micrographs. SB-10 reacts with cells in the outer aspect of the periosteal collar, while SB-20 and SB-21 react with a subset of cells present in the inner aspect of the collar.
Figure 2B:
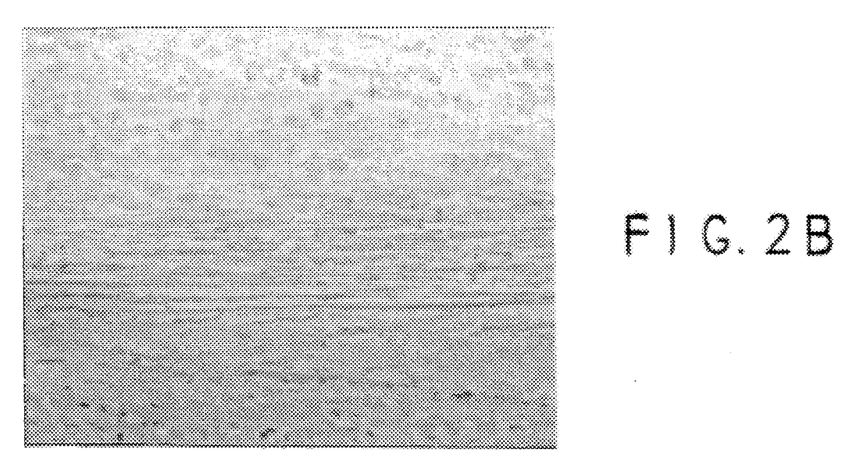
Figure 2C:
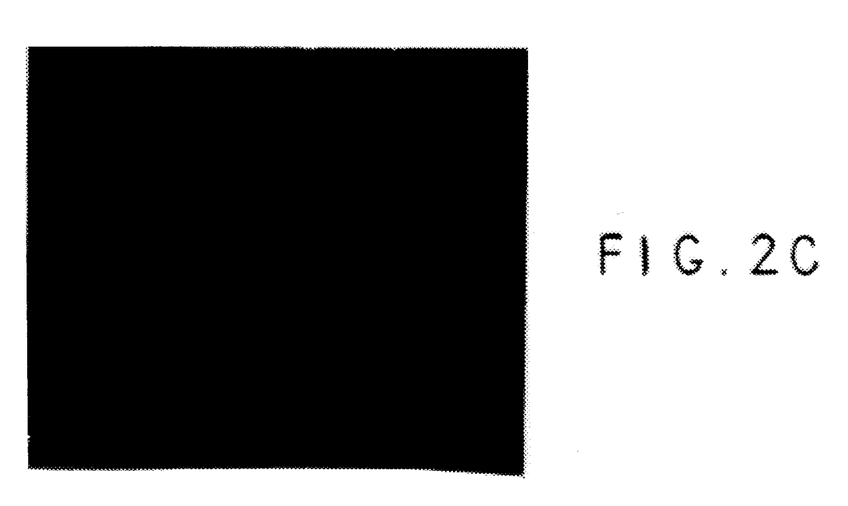
Figure 2D:
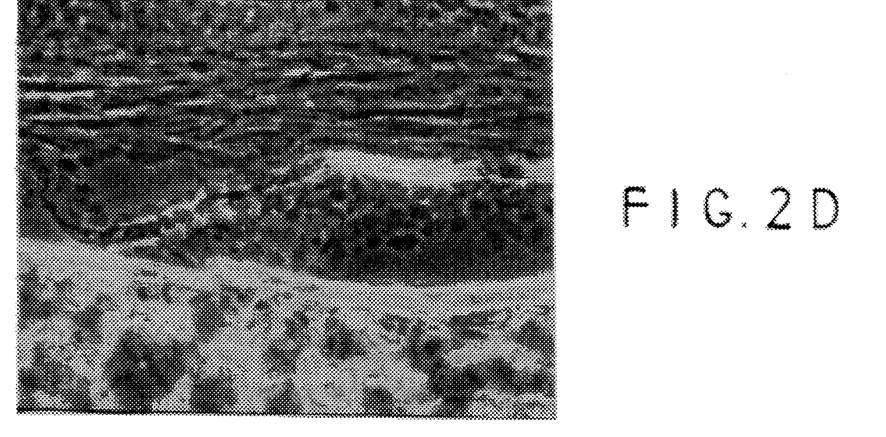
Figure 2E:
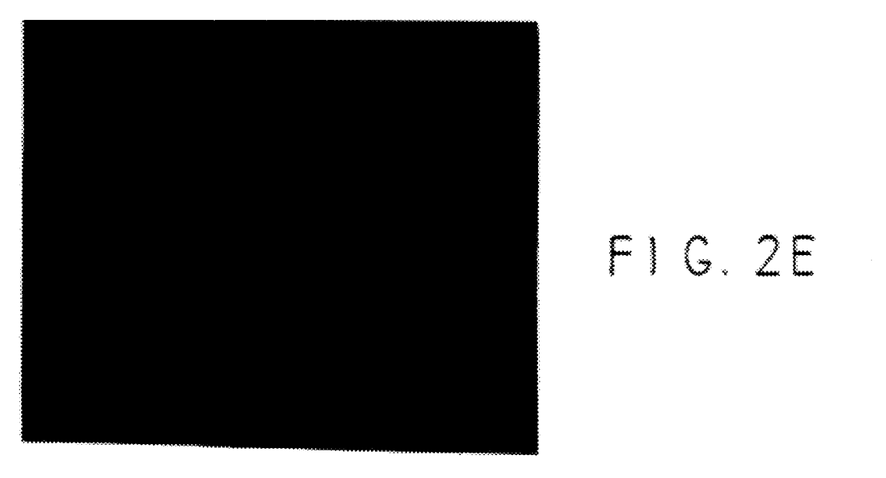
Figure 2F:
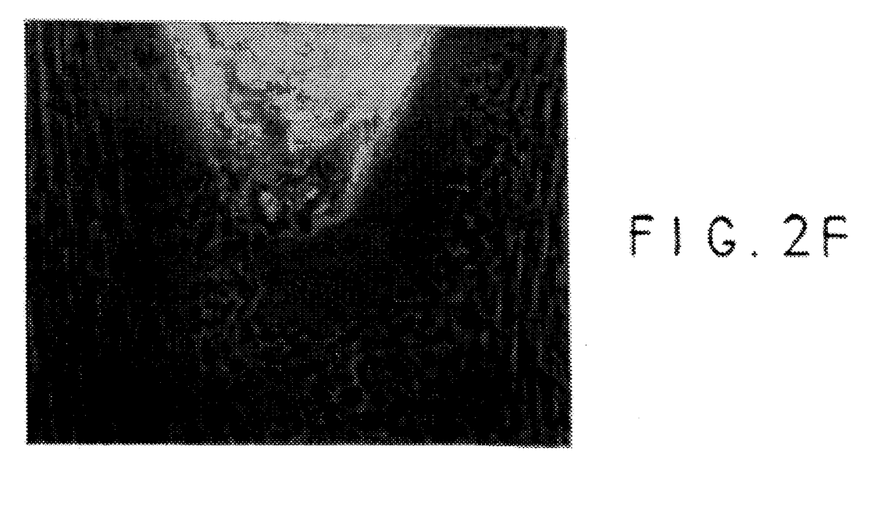

Critical analysis of these immunostained slides identified those antibodies which selectively bound to epitopes on normal human osteogenic cells. In addition, close observation of the staining pattern gave an indication of the cellular location of the antigen; intracellular, cell surface, or both. Of particular interest were the antibodies which reacted to the cell surface. Of the 224 wells which were selected on the basis of their semiquantitative cell-binding ELISA profile, 18 of these wells tested positive to osteogenic cells on frozen sections of embryonic human limbs. FIGS. 2A–2F are photomicrographs of typical frozen sections stained with antibodies SB-10, SB-20, and SB-21.

Antibody Binding to Cell Cultures

Indirect Immunofluorescent Staining

Culture dishes of living cells were rinsed three times with PBS. 100 μl aliquots of antibody culture supernatants were added to each dish and incubated for one hour at 4° C. in a humidified chamber. Dishes were rinsed three times with 0.1% BSA-PBS, then 100 μl of FITC-conjugated goat antibody specific for mouse IgG was added to each plate after being diluted 1:500 with 0.1% BSA-PBS. Dishes were incubated for one hour at 4° C. in a humidified chamber. Dishes were rinsed three times with 0.1% BSA-PBS and coverslipped after applying a drop of PPD immunofluorescent mounting medium. Immunofluorescent staining was observed using an Olympus B-Max epi-fluorescence microscope. The immunoreactivity of three monoclonal antibodies stained on various tissue culture preparations is reported in Table 3.

TABLE 3

Immunoreactivity of Selected Monoclonal Antibodies on Various Cells in Tissue Culture

| Cell Type | Antibody SB-10 | Antibody SB-20 | Antibody SB-21 |
|---|---|---|---|
| Embryonic (60 & 105 day) fibroblasts | +/− | − | − |
| Newborn Papillary fibroblasts | +/− | − | − |
| Adult Papillary fibroblasts | − | − | − |
| Newborn Reticular fibroblasts | +/− | − | − |
| Adult Reticular fibroblasts | +/− | − | − |

TABLE 3-continued

Immunoreactivity of Selected Monoclonal Antibodies on Various Cells in Tissue Culture

| Cell Type | Antibody SB-10 | Antibody SB-20 | Antibody SB-21 |
|---|---|---|---|
| SaOs-2 Osteosarcoma | +/− | − | − |
| MG-63 Osteosarcoma | +/− | − | − |
| Primary human osteoblasts | + | + | + |

Table 3. (−)=no immunoreactivity; (+/−), sparse or weak immunoreactivity; (+)=strong immunoreactivity.

IV. Cloning by Limited Dilution of Selected Colonies

The hybridomas which tested positive to each of the preliminary screens (i.e. the 18 wells) were cloned by the following process in order to ensure that the subsequent screening steps were performed on hybridomas which originated from a single clone. Since multiple cell lines are usually present in the original "parent" well, cloning of the cells was required to obtain a monoclonal hybridoma cell line. By replating cells at a density of less than one cell per well, any colony which grew in a well should be the progeny from only that cell. When all the growing daughter wells contained the antibody of interest for two serial clonings, the cell line was considered to be monoclonal. In addition, the cloning by limited dilution was also performed in order to reduce the risk of overgrowth by non-producer cells.

Preparation of Feeder Layer Cells and Conditioned Medium

Mouse splenocytes were used instead of macrophages at this stage. A mouse was sacrificed and its spleen was removed as described above. The cells were liberated as previously described, counted, and added to 37° C. Super HAT so that their concentration was 1 million per ml. When 96 well plates were used for plating, 0.1 ml of this suspension was added to each well. When 24 well plates were used for plating, 0.5 ml of this suspension was added to each well. Alternatively, this cell suspension was also grown in large culture flasks (20 ml) for up to three days. During those three days, the suspension was used to create feeder layers. If the cells were not used within the three days, the medium was collected by passing the suspension through a sterile 0.22 μm filter. This medium, which can be stored at 4° C. for several weeks, was a useful additive for poorly growing cultures. However, this medium was not used instead of feeder layers.

Cloning

In all of the cases below, the cells were plated into wells already containing a feeder layer (see above). The cells and medium were transferred from the selected parent wells of a 96-well plate to one well in a 24-well plate. 200 μl of medium was added back to the parent wells so that residual parent cells could continue to grow. The parent wells served as back-ups in case of error. Cell growth was monitored in the 24-well plate. It generally took about 3 to 7 days for a growing colony to cover half the well. In those wells which exhibited slow growth, additional conditioned medium was added. When the cells were growing nicely, the medium was again screened for antibody. Since there was no point in cloning these cells if they had stopped secreting antibody, this was a necessary step. If the antibody of interest was present, a small aliquot (50 μl) of cells was removed from the edge of the colony. This is normally where the most actively growing cells are found. 10 μl of this aliquot was added to 30 μl of 0.5% Trypan blue dye. The viable cells were counted and the dead cells appeared blue. The remaining 40 μl aliquot was manipulated so that 100 cells were removed with certainty. These 100 cells were added to 20 ml of Super HAT, the suspension was mixed and evenly plated into two 96-well plates. This resulted in two plates of cells at 0.5 cells per well. Colonies developed in about half of the wells within 5 to 10 days. The fast growing colonies were screened for antibody. When positive colonies were found by repeating the immunostaining, four of the colonies were transferred to new wells on a 24-well plate.

200 μl of medium was added back to the 96-well plate, and the new 24-well plate was treated exactly as the original 24-well plate above. This provided another source of back-up cells if cloning (or anything else) fails. Approximately 3 million cells were frozen per vial. Approximately two weeks after the fusion, the cells were switched from Super HAT to Super H+T medium. Cloning was continued using the above techniques until 100% of the subclones were positive for two generations. The successively more "clonal" cells were also frozen for precautionary measures. Once it was determined that a given cell line was monoclonal, the culture medium was changed to Hybridoma 20%. This medium, which allows for enhanced cell growth, consisted of 78 ml D-MEM, 20 ml FBS, 1 ml Glutamine (Gibco #320-5030), 1 ml Solution I (See above), 0.1 ml Gentamicin (M.A. Bioproducts #17-5187).

V. Recovering the Secreted Monoclonal Antibodies

The monoclonal antibodies secreted by the cloned hybridomas were recovered by either culturing the cloned hybridomas (individually) in the hybridoma medium and recovering the antibody from the medium, or culturing the cloned hybridomas intraperitoneally in mice and harvesting the ascites from the mice. In this regard, through the use of the following procedure, hybridoma cells grown in the peritoneal cavity of the mice produced an ascitic fluid rich in monoclonal antibodies.

The recipient mouse was "primed" 5 to 10 days prior to tumor cell inoculation by intraperitoneally injecting each mouse with 0.5 ml of Pristane (2, 6, 10, 14, Tetramethylpentadecane; Sigma, Catalog #T- 7640). The mice which were used to grow the tumors were of the same strain as that used to initially generate the hybridoma cell lines. The mice used were approximately 8 to 12 weeks of age. One tumor line was grown in 4–6 mice at a time. In culture, the established monoclonal cell line was grown in log phase and approximately 30 million cells were collected for innoculation. The cells were centrifuged at 1000 rpm for five minutes and then removed from the culture supernatant. Since the serum interferes with tumor production and contaminates ascites fluid, the cells were washed in serum-free medium and centrifuged again. The cells were resuspended in serum-free medium (i.e. DMEM-HG, Gibco, Grand Island, N.Y.) such that the final cell density was 10 million per ml. Using a 23 gauge needle, 0.5 ml (5 million cells) of the suspension were injected into the peritoneum of each recipient mouse. Approximately one week later, the mice appeared to have "bloated" abdominal cavities. Once they appeared to have enlarged to about the size of a plum, the ascites fluid present in the peritoneal cavity was tapped. During tapping the mice were lightly anesthetized using Metafane (Methoxyflurane; Pitman-Moore, Inc., Catalog #NDC 11716-5943- 4). Using a 22 gauge needle, the abdominal skin was pierced so that the needle was very superficially within the peritoneum. The ascites fluid then dripped out of the needle and into an awaiting vessel. By moving the mouse and/or the needle, it was possible to get as much as 5 mls of fluid. This fluid yielded antibody in the range of 0.5 to 5 mg/ml. The animals were placed back in their cages for recovery and further tapping.

In the animals which did not recover from anesthesia at any stage of the experiment, the residual ascites fluid was obtained by surgically opening the abdomen and removing pooled fluid. In this regard, it was important that the fluid was not collected from mice which had been dead for more than one hour. Once the fluid was collected, it was centrifuged at 3000 rpm for 5 minutes to pellet out the RBCs and other undesirable cells. Sodium azide was then added so that its final concentration was 0.02%. This ascitic fluid was then stored in small aliquots at minus 70° C. The stability of each antibody to freezing and thawing was tested before the entire ascites prep was frozen.

VI. Screening of Cloned Hybridomas

Selected hybridomas were screened against a series of mesenchymal and non-mesenchymal derived tissues to identify the degree of specificity of the monoclonal antibodies to normal human osteogenic cell subsets.

Screening Tissue Sections to Hybridoma Supernatants

The following tissues were obtained as surgical biopsies, therapeutic abortion tissues, or autopsy from human patients: skin, intestine, heart, skeletal muscle, lung, liver, brain, tendon, ligament, kidney, spleen, adrenal glands, pancreas, articular cartilage, periosteum, and intact embryonic limbs. The following animal tissues were also obtained for screening: chicken limbs, rabbit bone, rat limbs, canine bone, and bovine bone. The tissues were each embedded in OCT-Tissue Tek Freezing Medium (Miles Inc.) and frozen into blocks in liquid nitrogen and stored at −20° C. until use. The tissue blocks were sectioned at 6 micron thickness, placed on gelatine coated slides, and stored at −20° C. until use. Tissue sections were immunostained as described previously, and the results are outlined in Table 4.

The negative control in each experiment was achieved by incubating the cells or tissue of interest with SB-1, a monoclonal antibody to chicken alkaline phosphatase which does not react with human tissue, followed by rinsing, and then incubating with FITC-labelled secondary antibody. The test results of the three selected hybridomas, i.e. SB-10, SB-20, and SB-21 were evaluated against a control for background staining. The results are set forth below in Table 4.

TABLE 4

Immunoreactivity of Monoclonal Antibodies on Various Tissues

| Tissue Specimen | Antibody SB-10 | Antibody SB-20 | Antibody SB-21 |
|---|---|---|---|
| Species Cross-Reactivity | | | |
| Embryonic chick bone | – | – | – |
| Embryonic rat bone | – | – | – |
| Canine bone | – | – | – |
| Bovine bone | – | – | – |
| Rabbit bone | – | – | – |
| 50–85 day embryonic human tissues | | | |
| Adrenal gland | +/– | – | – |
| Kidney | +/– | – | – |
| Tongue | +/– | – | – |
| Intestine | +/– | – | – |
| Myocardium | – | – | – |
| Lung | + | – | – |
| Pancreas | – | – | – |
| Brain | – | – | – |
| Skin | +/– | +/– | +/– |
| Cartilage | +/– | – | – |
| Skeletal Muscle | – | – | – |
| Adult Human Tissues | | | |
| Brain | – | – | – |
| Liver | – | – | – |
| Kidney | – | – | – |
| Spleen | – | – | – |
| Foreskin | – | – | – |

Table 4. (–)=no visual immunoreactivity above control; (+/–)=minimal immunoreactivity above the control and for evaluation purposes was taken to be (–); and (+)=strong immunoreactivity above the control.

EXAMPLE 3

The Generation of Monoclonal Antibodies Against Human Osteogenic Cells Reveals Embryonic Bone Formation In Vivo And Differentiation of Purified Mesenchymal Stem Cells In Vitro It has been well-established that mesenchymal progenitor cells derived from bone marrow are capable of differentiating into osteoblasts. In addition, these mesenchymal stem cells (MSCs) also give rise to cartilage, tendon, ligament, muscle, and other tissues. However, knowledge of the steps involved in the commitment and differentiation of MSCs along these various lineages has been restricted, in part, by the lack of probes specific for cells at various stages within the osteogenic or other differentiation pathways. Since monoclonal antibodies are useful probes for studying differentiation, we immunized mice with intact living cell preparations of human bone marrow-derived MSCs induced into the osteogenic lineage in vitro. We screened hybridoma colonies against purified MSCs, MSCs undergoing osteogenic differentiation, and frozen sections of embryonic human limbs where long bones are developing around the cartilage rudiment. This screening protocol favors selection of antibodies which react with MSCs undergoing differentiation in vitro and human osteogenic cells in vivo. Using this approach, we have generated monoclonal antibodies against lineage stage-specific surface antigens on osteogenic cells derived from human marrow MSCs.

Using published techniques, MSCs were purified from 5 different patients (ages 28–46), culture expanded (29), and grown in DMEM-LG with 10% FBS and "Osteogenic Supplements" (100 nM dexamethasone, 50 μM ascorbic acid-2-phosphate, and 10 mM β-glycerophosphate. At days 3 and 6 of culture, early during alkaline phosphatase expression, and prior to mineralized nodule formation, the cells were liberated from the plates with 5 mM EGTA. Approximately 4 million 3 and 6 day cells were pooled for each of five weekly immunizations into Balbc/J mice. Using standard techniques, monoclonal hybridomas were produced, and culture supernatants were screened by a semiquantitative ELISA against purified MSCs, and MSCs cultured for 3 or 6 days with Osteogenic Supplements. Briefly, MSCs were plated on 96-well culture dishes, exposed to Osteogenic Supplements, and then reacted with culture supernatants followed by goat anti-mouse IgG conjugated to horseradish peroxidase. The secondary antibody was rinsed, and o-phenylenediamine substrate was added to the plates. Primary mouse monoclonal antibody binding was assessed by the colorimetric reaction quantified by scanning the wells at 490 nm on an ELISA plate reader. Colonies of interest were selected on the basis of differential binding to control MSCs and osteogenic cells derived from MSCs. Selected colonies were further screened by immunofluorescence on unfixed frozen sections of human embryonic limbs. Hybridoma colonies of interest were cloned and further immunocytochemical analyses were performed on a variety of normal and experimentally-derived tissues from human, rat, rabbit, chick, and bovine sources.

Nearly 10,000 hybridoma colonies were screened by the modified ELISA protocol described above. Based on differential binding to purified MSCs, or MSCs cultured for 3 and 6 days with Osteogenic Supplements, 224 colonies were selected for immunofluorescent screening against embryonic day 55–60 human limbs. The majority of those 224 colonies either reacted with multiple tissue types present in the developing limb, or were not detected in the developing bone. Thus far, 9 colonies have been identified which demonstrate specific immunoreactivity on cells of the osteogenic lineage. The patterns of reactivity vary; some hybridoma supernatants react with a large population of cells within the osteogenic collar and osteoprogenitor-containing periosteum, while others react with only those cells which appear to be actively involved in matrix synthesis. Two hybridoma colonies appear to react with osteogenic cells as well as hypertrophic chondrocytes. The results are summarized in Table 5.

TABLE 5

| Hybridoma Cell Line | Control MSCs | 3 day OS culture | 6 day OS culture |
|---|---|---|---|
| 20E8 | 0 | 1 | 8 |
| 13C9 | 0 | 1 | 3 |
| 5D9 | 0 | 1 | 2 |
| 18H4 | 0 | 3 | 5 |
| 18D4 | 0 | 2 | 4 |
| 10F1 | 0 | 0 | 2 |
| 13B12 | 0 | 4 | 2 |

Table 5 shows the immunoreactivity of selected hybridoma colonies against untreated MSCs, or MSCs cultured with Osteogenic Supplements (OS) for 3 or 6 days. Numbers reflect the relative amount of antibody bound in the ELISA assay described above.

These investigations indicate the presence of human osteogenic lineage stage-specific cell surface differentiation markers similar to those detailed for avian osteogenic cells. The staining of osteogenic cells in the developing limb supports the view that MSCs cultured with Osteogenic Supplements become "authentic" osteoblasts in culture. Osteogenic differentiation in vitro is thus confirmed by molecular probes which extend beyond traditional criteria of AP expression and mineralized nodule formation. Correlation of detailed in vitro observations with in vivo analyses of antigen expression will be useful in further studies of osteogenesis. Characterization of the specific tissue culture elements, i.e., bioactive factors, which promote progression of cells through the osteogenic lineage steps will be crucial. Identification of osteogenic cell surface, and/or extracellular matrix antigens should provide further insight into bone cell physiology. These and other monoclonal antibodies currently under investigation will prove useful in future studies of MSC differentiation.

The invention has been described with reference to the preferred embodiment. Modifications and alterations will occur to others upon reading and understanding the preceding detailed description. The invention includes all such modifications and alterations insofar as they come within the scope of the appended claims or equivalents thereof.

What is claimed is:

1. A hybridoma which produces monoclonal antibodies which react with the surface of normal human osteogenic cells, which hybridoma is selected from the group consisting of those having ATCC accession numbers HB-11789, HB-11790 and HB-11791.

2. A monoclonal antibody produced by the hybridoma of claim 1.

3. A method for detecting the presence of normal human osteogenic cell subsets in a sample comprising the steps of:

a) contacting said sample with the antibody of claim 2;

b) detecting the presence of normal human osteogenic cell subsets by reaction of the antibody with the sample.

4. A method of detecting the presence of a normal human osteogenic cell in a sample which comprises (a) contacting said sample with the antibody of claim 2;

(b) detecting the presence of a normal human osteogenic cell by reaction of the antibody with the sample.

5. A method for isolating a population of normal human osteogenic cells comprising the steps of:

(a) contacting a cell suspension containing normal human osteogenic cells with the monoclonal antibodies of claim 2; and (b) recovering cells that have reacted with the monoclonal antibodies from the cell suspension.

6. The method of claim 5 wherein the step of contacting comprises contacting the cell suspension with solid-phase linked monoclonal antibodies; and the step of recovering comprises recovering the bound cells from the unbound cells.

7. The method of claim 6 wherein the step of recovering further comprises recovering the bound cells from the solid phase linked monoclonal antibodies.

* * * * *